(12) United States Patent
Valdiserra et al.

(10) Patent No.: US 10,583,016 B2
(45) Date of Patent: Mar. 10, 2020

(54) EXTERNAL BREAST PROSTHESIS

(71) Applicant: NEW-TEAM, Bouloc (FR)

(72) Inventors: Christine Valdiserra, Reims (FR); Leonarda Comte Nee Sanchez, Bouloc (FR)

(73) Assignee: NEW TEAM, Bouloc (FR)

( * ) Notice: Subject to any disclaimer, the term of this patent is extended or adjusted under 35 U.S.C. 154(b) by 0 days.

(21) Appl. No.: 15/321,239

(22) PCT Filed: Jun. 11, 2015

(86) PCT No.: PCT/FR2015/051554
§ 371 (c)(1),
(2) Date: Mar. 3, 2017

(87) PCT Pub. No.: WO2015/197938
PCT Pub. Date: Dec. 30, 2015

(65) Prior Publication Data
US 2017/0189208 A1 Jul. 6, 2017

(30) Foreign Application Priority Data
Jun. 23, 2014 (FR) .................... 14 55791

(51) Int. Cl.
*A61F 2/52* (2006.01)
*A61F 2/12* (2006.01)
*A61F 2/50* (2006.01)

(52) U.S. Cl.
CPC ............ *A61F 2/52* (2013.01); *A61F 2/12* (2013.01); *A61F 2/5046* (2013.01); *A61F 2/50* (2013.01); *A61F 2/5044* (2013.01); *A61F 2002/5053* (2013.01)

(58) Field of Classification Search
CPC ........................................... A61F 2/12
See application file for complete search history.

(56) References Cited

U.S. PATENT DOCUMENTS 2,851,692 A 9/1958 Livingston et al.
3,189,921 A * 6/1965 Pangman .................. A61F 2/52
450/57

(Continued)

FOREIGN PATENT DOCUMENTS

BR 6801634 U 3/1990
EP 0 791 345 A1 8/1997

OTHER PUBLICATIONS

International Search Report dated Aug. 14, 2015, in corresponding PCT application.

*Primary Examiner* — Suba Ganesan
*Assistant Examiner* — Aren Patel
(74) *Attorney, Agent, or Firm* — Young & Thompson

(57) ABSTRACT

Disclosed is an external breast prosthesis (1), including an envelope (2) of flexible material with a breast shape, the envelope defining an internal cavity (6) closed by a protective lid (3) of which one face, called the external face (4), is designed to be pressed against the chest of a person, the cavity enclosing a filler and a weighted element intended to adjust the weight of the prosthesis. The weighted element is in the form of a plurality of ballast elements (7) which are distributed along a sagittal axis of the prosthesis substantially perpendicular to the plane of the protective lid.

11 Claims, 2 Drawing Sheets

(56) References Cited

U.S. PATENT DOCUMENTS

| | | | | |
|---|---|---|---|---|
| 3,278,947 | A | * 10/1966 | Silverman | A61F 2/52 |
| | | | | 450/57 |
| 3,811,133 | A | 5/1974 | Harris | |
| 4,125,117 | A | * 11/1978 | Lee | A61F 2/52 |
| | | | | 450/54 |
| 4,364,880 | A | 12/1982 | Howse | |
| 5,458,635 | A | 10/1995 | Berman | |
| 6,660,204 | B1 | * 12/2003 | Clover, Jr. | A61F 2/52 |
| | | | | 264/220 |
| 2005/0197698 | A1 | 9/2005 | Schneider-Nieskens | |
| 2008/0188787 | A1 | * 8/2008 | Clark | A61F 2/52 |
| | | | | 602/61 |
| 2008/0306590 | A1 | * 12/2008 | Hamilton | A61F 2/12 |
| | | | | 623/8 |
| 2013/0245758 | A1 | * 9/2013 | Chitre | A61M 39/0208 |
| | | | | 623/8 |

* cited by examiner

EXTERNAL BREAST PROSTHESIS

BACKGROUND OF THE INVENTION

Field of the Invention

The invention relates to an external breast prosthesis, and more particularly to such a prosthesis, non-functional, intended to temporarily replace a breast having been subject to ablation and the aspect and the dynamic behavior of which is as close as possible to that of the original breast.

External breast prostheses are generally used after mastectomy, after healing and before a surgical reconstruction of the breast, i.e. during a period of generally two years. An external breast prosthesis may be made tailored for a given patient, which generally involves a significant cost, or else be selected from a selection of standard prostheses, which are more economical. However, in this case, certain adjustments, such as the weight of the prosthesis which has to be substantially equal to the weight of the remaining breast (in the case of a one-sided mastectomy) are not achieved and may in the long run generate complications such as scoliotic attitudes or generate discomfort for the patient.

Description of the Related Art

For example from document U.S. Pat. No. 3,811,133 an external breast prosthesis is known including a hollow shell in a synthetic material, for example in flexible vinyl, breast-shaped, a fiberfill and a variable weight element consisting of metal granules, for example lead bound in a block of synthetic material or in a container in sewn felt. This weight is placed as close as possible to the chest of the patient, either attached or immobilized on a rear wall of the shell pressed against the chest of the patient. This type of prosthesis, which is related to tailored prostheses, nevertheless has many drawbacks. For example, the fiberfill used does not allow the prosthesis to have a dynamic behavior comparable with that of a natural breast which may be particularly visible during the use of the prosthesis with lightweight clothes such as a flexible bra.

BRIEF SUMMARY OF THE INVENTION

The present invention therefore aims to provide an external breast prosthesis which does not have the drawbacks of the known prostheses of the prior art.

In particular, the invention aims at providing such a prosthesis for which the weight is adjustable by the user.

The invention also relates to such a prosthesis which has a dynamic behavior closer to a natural breast.

The invention further aims at such a prosthesis for which the cantilever torque is adjustable.

The invention further aims at such a prosthesis for which the manufacturing cost is close to that of a standard prosthesis while providing the comfort and the esthetics of a tailored prosthesis.

To do this, the invention relates to an external breast prosthesis, comprising a shell in a flexible material having a breast-shape, said shell defining an internal cavity closed by a lid, for which one face, called external face, is adapted so as to be pressed against the chest of a person, said cavity containing a fiberfill and a weight element intended for adjusting the weight of the prosthesis, characterized in that the weight element is made in the form of a plurality of ballast elements distributed along a sagittal axis of the prosthesis substantially orthogonal to the plane of the lid.

In the present description, the terms conventionally used in the medical field in physiology for defining the different orientations in space relatively to the body of a patient, are used, in this case the planes (frontal, sagittal, horizontal planes) or axes (sagittal or antero-posterior axis orthogonal to the front plane; transverse axis orthogonal to the sagittal plane and vertical axis orthogonal to the horizontal plane). These terms taking as a reference the body of a patient, the horizontal plane relatively to the body may be vertical relatively to the earth's surface if the body is in a laid position.

By using a plurality of ballast elements distributed in the sagittal axis of the person bearing the prosthesis, it is not only possible to adjust the total weight of the prosthesis so as to have it match that of the missing breast or of the other breast, but also to modify its cantilever torque so as to retain a sensation closer to that of the original in the movements of the body, and this, even if this torque is compensated by the bra. Also, the displacement and/or the shape modification of the prosthesis during these movements are closer to that of a natural breast for which the dynamic behavior depends on the distribution of its mass in all the directions, notably along the sagittal axis.

Advantageously and according to the invention, the internal cavity has an interior shape, the contour of which along a section through a front plane is curvilinear, notably a substantially circular, elliptical or oval contour. For example, the internal cavity has a substantially frusto-conical shape, with a height oriented along a sagittal axis. This shape gives the possibility of using ballast elements having a shape of discs (or discoids) placed orthogonally to the sagittal axis of the prosthesis. It is also possible to select an internal cavity having the shape of a spherical cap which has similar advantages.

Advantageously and according to the invention, the cavity is adapted for containing from three to five ballast elements of staged sizes, decreasing from the lid to the distal end of the cavity. In order to obtain a good distribution of the cantilever torque of the prosthesis, it is advantageous to provide that the cavity may contain a sufficient number of ballast elements and that these elements may be ordered in the cavity. The inventors notice that a satisfactory result is obtained with three to five elements for which the sizes (in this case the diameters) are staged so that their edge comes into contact or in close proximity to the wall of the cavity, according to a predetermined order (the smallest at the distal end of the cavity).

Advantageously and according to the invention, for each size of a ballast element, there exists a plurality of ballast elements having different weights. In this way, it is possible for the user to produce the optimum distribution of the cantilever torque by selecting the weight of each ballast element depending on its position along the sagittal axis of the prosthesis. It is thus possible to act by means of the elasticity of the shell and by a suitable selection of the ballast elements, on the general shape of the breast in a sagittal or vertical plane, for example in order to obtain a "heavy" (low) breast by selecting ballast elements with a larger weights in a distal position or else a high breast by placing the heaviest ballast elements in a proximal position.

Advantageously and according to a first embodiment of the invention, the ballast elements are weighted discs inserted into parallel slots made in a foam fiberfill adjusted to the shape of the internal cavity. By the use of a foam fill, preferably very flexible, provided with parallel slots orthogonal to the sagittal axis of the prosthesis, each section of the fiberfill, on either side of a slot, may be moved relatively to the adjacent sections under the effect of static or dynamic stresses related to the weight of the weighted disc inserted into the slot. These discs may be metal discs of different densities or discs of synthetic material loaded with particles of different densities or with particles of the same density in different proportions. Preferentially, the weighted discs are immobilized in their slot, either through suitable raised/recessed portions, or by the shape of the slot which is closed above the disc once the latter is inserted.

Advantageously and according to a second preferential embodiment of the invention, the ballast elements are ballast pads with a substantially lenticular shape, the main median plane of which is substantially parallel to the plane of the lid. By thus using lenticular pads, i.e. having a tangible thickness, preferably corresponding to a fraction of the depth of the cavity, it is possible to omit the foam fill of the previous embodiment, the thickness of each of the pads contributing to the filling of the cavity of the prosthesis. The size (for example the diameter for a pad of a circular shape) is adapted, as seen earlier, for coming into contact with the internal wall of the cavity depending on the rank of the pad on the sagittal axis of the prosthesis.

Advantageously and according to the invention, each ballast pad comprises an external wall with the shape of a flexible pouch filled with a deformable load. Each pouch may be formed by the gathering of two sheets of flexible synthetic material, for example in an elastomer, welded together with their edges facing each other along a substantially circular, elliptical or oval contour depending on the shape of the cavity of the prosthesis (orthogonally to the sagittal axis of the latter). Inside each pouch, a filling load gives the possibility of giving its lenticular shape to the pouch. The load is preferably plastic, i.e. deformable and having reduced or zero elasticity.

Advantageously and according to the invention, the deformable load consists of a divided solid with a specific density adapted to the sought weight. For example, the deformable load may be formed with a granulate of solid material, for example microbeads with a diameter from 10 µm to 500 µm. Such glass microbeads may have an apparent specific density ranging from 0.2 kg/dm$^3$ for hollow beads up to 1.5 kg/dm$^3$ for solid beads. For pads of a higher weight, it is possible to use metal microspheres which have greater densities or mixtures of different types of granulates.

Advantageously and according to the invention, the deformable load consists of a polymeric gel including a load, the density of which depends on the sought weight. Preferentially, in order to improve the tactile sensation which is felt, it is possible to integrate the divided solid load into a binder such as a polymeric gel in order to obtain a viscoelastic load in a single piece. The specific density of this deformable load is then determined by the specific density of the gel, that of the solid load and by the solid load proportion in the gel.

Advantageously and according to the invention, the ballast pads include attachment means placed on a sagittal axis of the prosthesis and adapted for making secured faces facing both adjacent pads. Thus, each ballast pad may be made secured to the adjacent pads while retaining a certain mobility brought by the relative movement of both sheets forming the faces of the pouch. In this way, the assembly of the pads behaves like a flexible viscoelastic mass having the capability of tilting on either side of the sagittal axis depending on the movements of the bust of the user, like a natural breast.

Advantageously and according to the invention, the prosthesis further includes a disc of elastic material adapted so as to be placed between the lid and the ballast pads for maintaining the latter in compression. Depending on the sought weight and dynamic behavior, it is not necessary to use all the pads of a prosthesis. For example, it is possible to only use three ballast pads on the five which the shell of the prosthesis may receive. It is then possible to use a filling buffer in synthetic foam placed between the pads and the lid forming the rear face of the prosthesis in order to maintain the pads in place, with a minimum of compression in order to avoid any movement of the ballast pads which may be expressed by an unsightly shape of the prosthesis.

Advantageously and according to the invention, the shell is made in a thermoformed thermoplastic foam, notably selected from among polyolefin foams, in particular in a thermoformed polyethylene foam. In addition to the flexible synthetic materials currently used for producing external prosthesis, such as silicone, latex or vinyl, the invention proposes the use of a polyethylene shell, preferably in low density polyethylene for its flexibility. Still more advantageously, the shell may be made in a polyethylene foam which has the advantage of being very light weight and of being thermoformed to the desired shape by more economical production operations than those used for the other materials. Further, such a thermoformed polyethylene foam has the advantage of providing a surface which is very soft to the touch, even closer to the tactile sensation of the skin than the other materials.

Advantageously and according to the invention, the shell is tinted in the bulk and includes an added nipple. Further, the polyethylene foam has the advantage of being able to be tinted in the bulk and of having at least on one face a "skin" aspect. Further, in order to take into account the different complexion hues, it is possible to produce a nipple and its adjacent areola in another foam tint and to add it for example by adhesive bonding on the shell. Advantageously, in this case, the foam used may have a greater density in order to provide better resistance to abrasion in this area strongly subject to friction.

Advantageously and according to the invention, the shell includes at least one opening of the cavity allowing the introduction of the ballast elements. The opening of the cavity is preferentially produced by a separation between the edge of the lid and that of the shell, on an upper portion of the contour of the latter along the front plane of the prosthesis. For example, one of the two surfaces facing the edge of the lid or of the shell includes a double-sided adhesive tape, if necessarily reusable, giving the possibility of closing the cavity after introducing the ballast elements.

Advantageously and according to the invention, the lid includes, on its external face, an attachment strip covered with a plurality of detachable protective films juxtaposed so as to allow the selection of at least one adhesive bonding area on the chest. Although the external breast prosthesis according to the invention is provided so as to be worn inside a bra, it is however preferable that it be attached to the chest of the user. For this purpose, the invention provides that the lid, on its external face in contact with the chest, includes an adhesive tape, for example a biocompatible double-sided adhesive tape which is resistant to water and other current washroom products. The adhesive tape is originally attached on the external face of the lid and includes facing the chest of the user a plurality of protective films which may be removed in order to ensure adhesive bonding on the chest. The protective films are positioned so as to allow the user to select the areas for adhesive bonding of the prosthesis depending on the arrangement of particular sensitivity areas (for example scars, etc).

BRIEF DESCRIPTION OF THE DRAWINGS

The invention also relates to an external breast prosthesis characterized by combination of all or part of the features mentioned above or hereafter.

Other objects, features and advantages of the invention will become apparent considering the description which follows and the appended drawings wherein.

DETAILED DESCRIPTION OF THE PREFERRED EMBODIMENTS

Figure 1:
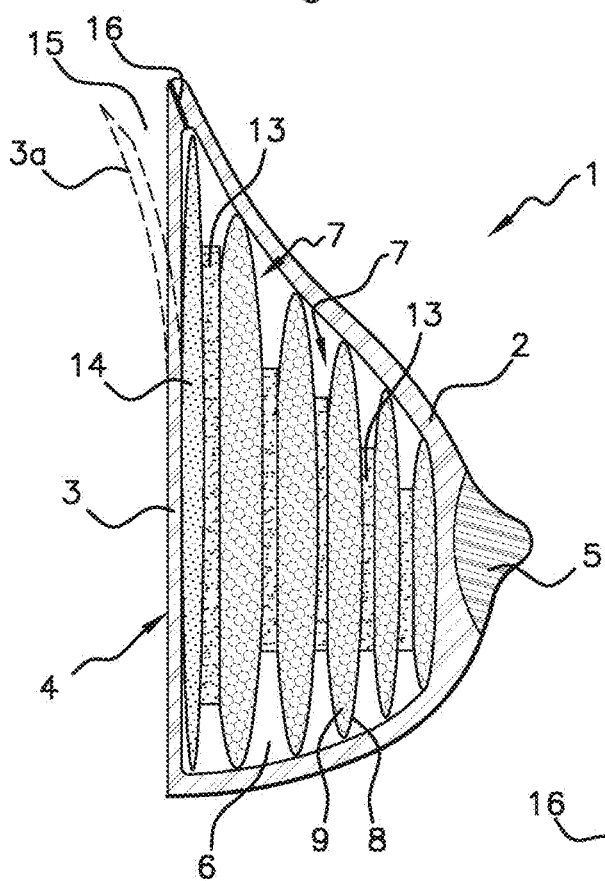
FIG. 1 is a schematic sectional view through a median sagittal plane of an external breast prosthesis according to a preferential embodiment of the invention.

The external breast prosthesis 1 illustrated in FIG. 1 includes a shell 2 with the shape of a breast made in a supple and flexible material, preferentially in low density polyethylene foam with a thickness varying between 3 mm and 10 mm.

The shell 2 defines an internal cavity 6 closed by a substantially plane lid 3. The lid 3 may be made in a single piece with the shell 2 or else be stuck or welded on the contour of the shell 2 in order to close the cavity 6. In one case like in the other, an opening 15 of the cavity is made in the upper portion of the contour of the shell in order to allow the introduction of ballast elements and of the filling elements into the cavity. The opening 15 is obtained by separating a portion 3a (illustrated in dash lines in FIG. 1) of the lid 3 from the contour of the shell 2. It may be closed by adhesive bonding by means of a reusable adhesive closure 16.

In the preferential embodiment illustrated in FIG. 1, the cavity 6 contains five ballast elements as ballast pads 7 of a lenticular shape and with staged sizes. The pads 7 are positioned so that their median plane is substantially orthogonal to the sagittal axis of the prosthesis 1, parallel to the lid 3. Each pad 7 is of a suitable size (in this case a diameter) in order to correspond to the internal diameter of the cavity 6 depending on its position on the sagittal axis. For example, the pad 7 placed at the distal end of the cavity 6 has the smallest diameter.

The ballast pads 7 include an external wall forming a flexible pouch 8 containing a deformable load 9. The pouch 8 may be produced by joining along their edge, two discs of flexible synthetic material, for example in elastomer. Before complete joining, the pouch 8 is filled with a load 9 which gives it its thickness and therefore its lenticular shape. The load 9 may consist of a powder or of granules, for example glass beads, which, in combination with the elasticity of the pouch 8, give a viscoelastic consistency to the pad 7, the consistency being related to the natural consistency of the breast. Alternatively, the pouches 8 may be filled with a polymeric gel, for example a silicone hydrogel alone or being used as a binder to a granular load.

According to the invention, for each pad size 7, there exists a plurality of pads 7 having a different weight in order to give the possibility, for a given total weight corresponding to the weight of the replaced breast, of having several solutions for distributing the weight along the sagittal axis. For a same pad size, the different weights may be obtained by acting on the density of the gel, on the density (real or apparent) of the granular load, on the load proportion in the gel, etc. For example, a granular load formed with hollow glass microbeads may have an apparent density ranging from 0.2 to 1.5. Greater densities may be obtained with microbeads of another material, for example metal microbeads. Depending on the size and therefore on the volume of the pad, all the ranges of weights may be obtained by producing if required mixtures of different loads. Of course, the different loads are not limited to the mentioned microbeads but may comprise talcs or any other type of load known to one skilled in the art.

The pads 7 further include means for attachment between adjacent pads. In the example illustrated in FIG. 1, these attachment means are adhesive tabs 13, positioned along the sagittal axis. These adhesive tabs 13 are of course reusable for allowing changes in the pads depending on the intention of the user. These adhesive tabs have a diameter less than the diameter of the pads which they connect in order to leave clear a ring shaped area of each face of the pouch 8 in order to allow a lateral displacement of each pad relatively to the adjacent pads by deformation of this ring shaped area of the pouch.

In order to maintain the ballast pads 7 in the cavity 6, a filling buffer 14, in an elastic material of a suitable shape, for example a cylinder in elastic foam, ends the stacking of the pads and is used as a spring between the lid 3 and the largest pad in order to retain the pads in compression.

The shell 2 of the prosthesis 1 may be made in a single piece. However, according to the invention, it may be preferable to provide addition of an insert 5 forming the nipple and the peripheral areolar area for allowing a suitable change in tint on the one hand, the nipple and the areola being generally of a darker complexion than the remainder of the breast and using a material more resistant to abrasion on the other hand, taking into account that this area is much more subject to friction stresses. The added nipple may be attached by adhesive bonding or else by cooperation of conjugate shapes during the thermoforming of the shell 2.

Figure 3:
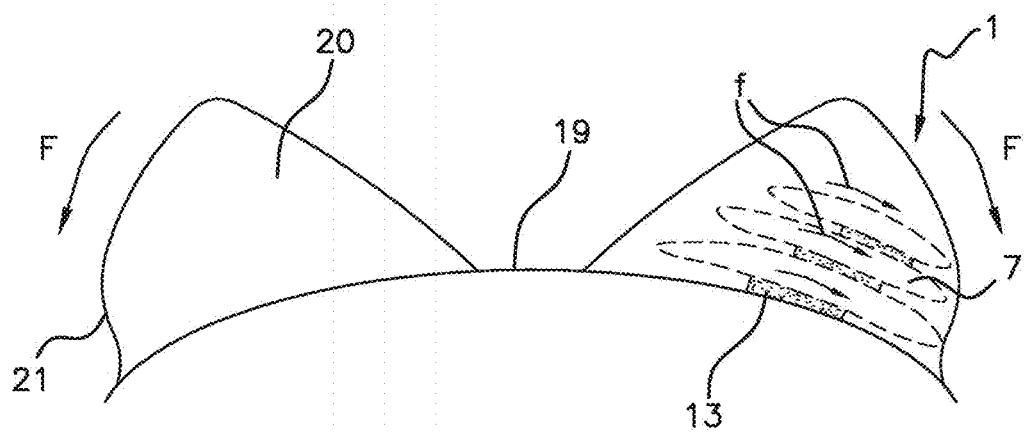
FIG. 3 is a view along the vertical axis of a breast of a laid-down person comprising a natural breast and a prosthesis according to the invention, illustrating the static and dynamic reality mechanism of the prosthesis.

Reference is made to FIG. 3 for detailing one of the advantages of the prosthesis according to the invention. In this figure, a chest comprising a natural breast 20 and a prosthesis 1 in a laid-down position, seen along an axis corresponding to the vertical axis of the body is illustrated in this figure. In the laid-down position, the natural breast 20 tends to move outwards relatively to the chest 19 (a movement illustrated by the arrow F), and to form a curve 21. In the prosthesis of the prior art, the filling with a constant density and the place of the weight as close as possible to the chest cause that the prosthesis remains immobile and rigid. For the prosthesis 1 according to the invention, the inventors noticed that the whole of the pads 7 behaves like a flexible viscoelastic mass by means of the distribution of weight along the sagittal axis and of the deformation of each pad 7, the anterior and posterior faces of which of the pouch laterally sliding relatively to each other while being maintained with the adhesive tab 13 respectively to the corresponding face of the adjacent pad. This relative sliding of the pads 7, illustrated by the arrows f in FIG. 3, causes a deformation of the shell 2 along an arrow F similar to that of the natural breast and causes a similar curve. Also, many movements of the chest are made possible by the prosthesis according to the invention and the comfort feeling of the user is reinforced.

Figure 2:
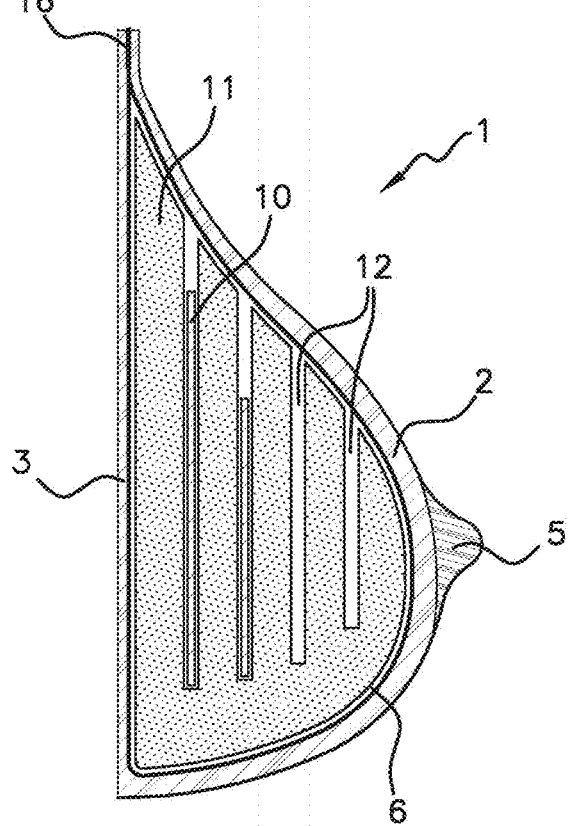
FIG. 2 is a sectional view along the same plane as FIG. 1 of a prosthesis according to another embodiment.

Another embodiment of the prosthesis 1 is illustrated in FIG. 2. In this embodiment, the cavity 6 of the shell 2 is filled with a foam fill 11 adjusted to the shape of the cavity. The ballast elements appear as weighted discs 10 inserted into slots made in the filling 11. Each slot 12 has, depending on its rank on the sagittal axis, a contour corresponding to the contour of the disc 10 corresponding to this rank, except for the area for inserting the disc in the upper portion of the filling. The size of the discs 10 is adapted for allowing a foam thickness right around the disc so as not to have any influence on the tactile sensation. The foam forming the filling 11 is sufficiently flexible for allowing a relative lateral movement of the disc 10 with respect to each other, thereby allowing dynamics of the prosthesis similar to those obtained with the pads.

For each disc size, a plurality of discs 10 of different weights is provided thereby allowing modulation of the torque exerted on the shell 2 depending on the cantilever of the prosthesis. In this embodiment, the shell 2 also includes an opening allowing insertion of the filling 11 and of the discs 10 into the cavity, an opening closed by an adhesive closure 16. The shell 2 may also include an added nipple 5.

Figure 4:
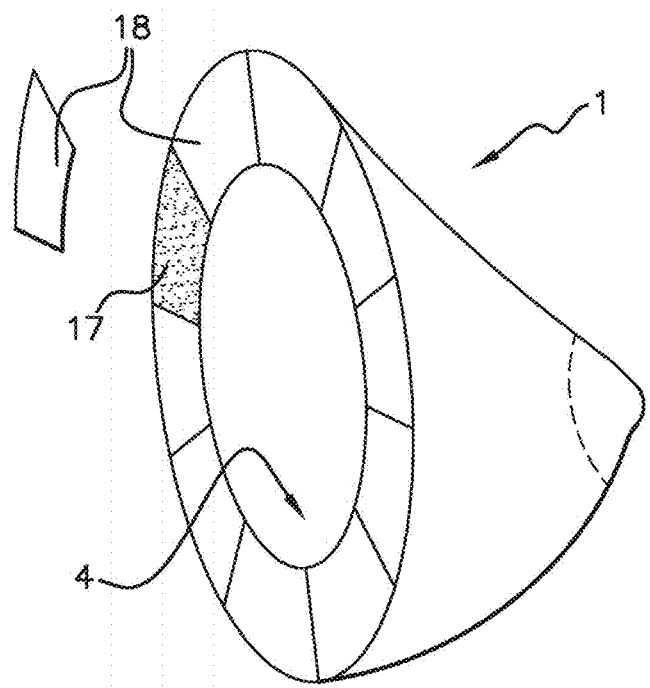
FIG. 4 is a perspective three-quarter rear view showing the external face of the lid and the adhesive tape allowing attachment of the prosthesis according to the invention on the chest of a person.

Regardless of the embodiment of the prosthesis according to the invention, the latter includes means for attaching the prosthesis on the chest of a user. These means are illustrated in FIG. 4 and in include, on the external face 4 of the lid 3 an attachment strip 17, for example consisting of a biocompatible double-sided adhesive. This attachment strip 17 has a suitable shape for following the contour of the lid 3 and a sufficient width for allowing adapted attachment of the prosthesis on the chest of the user. Advantageously, this attachment strip is covered with a plurality of detachable protective films 18 juxtaposed covering the whole surface of the attachment strip 17. This advantageous arrangement allows the user to select the area for adhesively bonding the prosthesis on her chest so as to avoid areas of particular sensitivity such as scars, etc. The attachment strip 17 may be advantageously water-resistant and resistant to current washroom products so as to be able to be permanently worn.

Of course, this description is given only as an illustrative example and one skilled in the art may provide thereto many modifications without departing from the scope of the invention, such as for example modifying the location of the opening 15 of the shell 2 in any area of the contour of the lid 3 or even at the center of the latter. Also, the filling buffer 14 in the embodiment of FIG. 1 may be equivalently placed at the distal end of the cavity 6 while ensuring its spring function.

The invention claimed is:

1. An external breast prosthesis (1) comprising:
a shell (2) in a flexible material, the shell having a lid part attached to a second part, the lid part having an external face (4) that presses against an external surface of a chest of a person, the second part having an external side with an external shape that matches an external contour of a breast shape, the lid being attached to an upper part of the second part and to a lower part of the second part, the lid extending along a plane between the upper part of the second part and the lower part of the second part,
the lid having an internal side that together with an internal side of the second part defines an internal cavity (6) within the shell,
the shell including a closable opening which allows access to the internal cavity;
a plurality of ballast elements (7, 10) located within the internal cavity, the plurality of ballast elements (7, 10) being adjustable for adjusting a weight of the prosthesis,
wherein,
the plurality of ballast elements (7, 10) distributed along a sagittal axis of the prosthesis orthogonal to the plane of the lid,
a thickness between the external side and the internal side of the second part of the shell is between 3 mm and 10 mm,
the closable opening is a separateable portion (3a) located where the lid (3) is attached to the second part of the shell,
each of the ballast elements comprise a ballast pad (7) of a lenticular shape, each ballast pad including an external wall forming a flexible pouch (8) containing a deformable load (9);
plural adhesive elements (13) that fix each ballast pad to an adjacent ballast pad so that the ballast elements are fixed one to another, each adhesive element being positioned along the sagittal axis, the adhesive tabs being reusable for allowing changes in the ballast pads and thereby adjusting the weight of the prosthesis; and
a filling buffer (14) of an elastic material located between the internal side of the lid and a first one of the ballast pads (7), the filling buffer (14) providing a spring between the lid (3) and the first one of the ballast pads (7) in order to retain the ballast pads in compression.

2. The prosthesis according to claim 1, wherein the internal cavity (6) has an interior shape, the contour of which along a section through a front plane is curvilinear, having a circular contour, an elliptical contour, or an oval contour.

3. The prosthesis according to claim 2, wherein the cavity (6) is adapted for containing from three to five of the ballast elements (7, 10) of staged sizes, decreasing from the lid (3) to a distal end of the cavity.

4. The prosthesis according to claim 1, wherein the cavity (6) is adapted for containing from three to five of the ballast elements (7, 10) of staged sizes, decreasing from the lid (3) to a distal end of the cavity.

5. The prosthesis according to claim 4, wherein, for each size of a ballast element (7, 10), there exists a plurality of ballast elements having different weights.

6. The prosthesis according to claim 1, wherein the deformable load (9) consists of a divided solid with a specific density adapted to a sought weight.

7. The prosthesis according to claim 1, wherein the deformable load (9) consists of a polymeric gel including a load, the density of which depends on a sought weight.

8. The prosthesis according to claim 1, wherein the ballast pads (7) include attachment means (13) placed on a sagittal axis of the prosthesis and adapted for making faces secured to each other facing two adjacent pads.

9. The prosthesis according to claim 1, wherein the shell (2) is made in a thermoformed thermoplastic foam, selected from among polyolefin foams.

10. The prosthesis according to claim 1, wherein the shell (2) is tinted in bulk and includes an added nipple (5).

11. The prosthesis according to claim 1, wherein the lid (3) includes, on its external face (4) an attachment strip (17) covered with a plurality of juxtaposed detachable protective films (18) so as to allow the selection of at least one area for adhesive bonding on the chest.

\* \* \* \* \*